(12) United States Patent
Prior et al.

(10) Patent No.: US 6,663,779 B2
(45) Date of Patent: Dec. 16, 2003

(54) AUTOCLAVABLE ANNULAR CHROMATOGRAPH

(75) Inventors: Adalbert Prior, Gotzis (AT); Joachim Prior, Graz (AT); Juergen Wolfgang, Horbranz (AT)

(73) Assignee: Prior Separation Technology GmbH, Goetzis (AT)

( * ) Notice: Subject to any disclaimer, the term of this patent is extended or adjusted under 35 U.S.C. 154(b) by 0 days.

(21) Appl. No.: 10/019,654

(22) PCT Filed: Feb. 24, 2001

(86) PCT No.: PCT/EP01/02122
§ 371 (c)(1),
(2), (4) Date: Feb. 19, 2002

(87) PCT Pub. No.: WO01/67088
PCT Pub. Date: Sep. 13, 2001

(65) Prior Publication Data
US 2002/0153321 A1 Oct. 24, 2002

(30) Foreign Application Priority Data
Mar. 7, 2000 (EP) .............................................. 00104868

(51) Int. Cl.$^7$ .............................................. B01D 15/08
(52) U.S. Cl. ...................... 210/657; 210/656; 210/659; 210/198.2
(58) Field of Search .................. 210/635, 656, 210/657, 659, 198.2

(56) References Cited

U.S. PATENT DOCUMENTS

| | | | |
|---|---|---|---|
| 3,257,781 A | | 6/1966 | Debbrecht et al. ............ 55/197 |
| 5,023,061 A | * | 6/1991 | Snyder ........................ 423/70 |
| 5,024,749 A | * | 6/1991 | Snyder .................... 210/198.2 |
| 5,045,209 A | * | 9/1991 | Snyder ........................ 210/656 |
| 5,098,678 A | * | 3/1992 | Lee et al. ..................... 423/70 |
| 5,110,566 A | * | 5/1992 | Snyder ........................ 423/70 |
| 5,124,023 A | * | 6/1992 | Bosserman ................. 210/657 |
| 5,133,869 A | * | 7/1992 | Taniguchi ................... 210/656 |
| 5,149,436 A | * | 9/1992 | Taniguchi ................... 210/657 |
| 5,183,548 A | | 2/1993 | Snyder et al. .......... 204/299 R |
| 5,470,479 A | * | 11/1995 | Snyder .................... 210/198.2 |
| 6,391,196 B1 | * | 5/2002 | Prior ....................... 210/198.2 |

FOREIGN PATENT DOCUMENTS

| | | | | |
|---|---|---|---|---|
| JP | A 6-281639 | 10/1994 | ............. | 210/198.2 |
| WO | WO 98/45699 | 10/1998 | ............. | 210/198.2 |
| WO | WO 99/12625 | 3/1999 | ............. | 210/198.2 |
| WO | WO 99/47913 | 9/1999 | ............. | 210/198.2 |

\* cited by examiner

Primary Examiner—Ernest G. Therkorn
(74) Attorney, Agent, or Firm—Oliff & Berridge, PLC

(57) ABSTRACT

A continuous annular chromatography (CAC) device is disclosed including a stationary column head, a stationary eluate ring, a rotating body which is located between said column head and said collecting ring and which can rotate about a vertical axis and contains a chromatographic separating medium and a drive device. An extension can be coupled to a drive shaft of the drive device with a rapidly detachable connection.

20 Claims, 3 Drawing Sheets

AUTOCLAVABLE ANNULAR CHROMATOGRAPH

REFERENCE TO RELATED APPLICATIONS

This application is a 371 of PCT/EP01/02122 filed Feb. 24, 2001.

The invention relates to a device for continuous annular chromatography sterilizable in an autoclave, and to a method for using the device.

From WO 99/12625, an annular chromatograph is known which has a stationary eluate collecting ring formed as a slide ring on which a rotating body comprising the chromatographic gel particle bed in the shape of a cylinder jacket and an integrated bottom plate is slidingly and sealingly guided. The purpose being to protect continuous annular chromatography (international abbreviation CAC) performed with this device against contamination by the environment and to enable sterile work. Collecting points in the form of chambers with liquid withdrawal are arranged in the eluate collecting ring. Channels receiving the fractions draining from the particle bed of the CAC column and conveying them to the chambers of the eluate collecting ring are present in the bottom plate.

Particularly for separations of biological or biochemical materials and in applications for the working up of pharmaceutically active substances, the requirements for a chromatographic process free of contamination are stringent. Systems closed toward the outside are required here which are readily sterilized and in addition are readily adapted to changing separation jobs, while it must be remembered that the device that is to be operated free of contamination consists of rotating and stationary parts. In addition, a need exists for provisions being taken during eluate withdrawal that the discharge of the eluate or fractions from the particle bed and the chambers in the collecting ring be as uniform as possible and at the same time the separation as sharp as possible. Moreover, appropriate measures should be taken so that fractions already separated will not later be "spread" to neighboring chambers.

According to WO 99/12625, the desire for improved discrimination in the separation was met by design, by raising the number of channels in the bottom plate and of chambers in the collecting ring to a maximum that was technically feasible and represented an economically meaningful maximum. The resulting problems caused by effects of adhesion and capillarity due to the reduced cross sections of the channels in the bottom plate and particularly of the liquid withdrawal ducts of the collecting ring chambers were solved by increasing the diameter of the channels in the bottom plate radially upward toward the particle bed so as to make them wedge-shaped. The chambers were additionally provided with pressure equalization ports that for sterile operation can be covered up by suitable sterile filter membranes, in order to prevent the development of underpressure and resulting aspiration of nonsterile foreign air into the chambers via the slide ring packing.

The undesired spreading of parts of the fractions into neighboring chambers of the collecting ring was reduced according to WO 99/12625, primarily by selecting a diameter of the channels in the bottom plate that was considerably larger than the thickness of the radial walls between the chambers of the collecting ring. The liquid stream arriving from a channel is then cut off by the radial walls as with a shear blade when the channel slides over such a radial wall, so that the liquid column existing between channel and chamber which is important for a regular liquid drain and which is substantially thicker than the radial wall between two neighboring chambers, is interrupted only in part but never over its entire cross section.

The present invention which primarily represents a development of the CAC device from WO 99/12625 but is not restricted to the features of this document refers to a device for annular chromatography with a stationary column head, a stationary eluate collecting ring, a rotating body between head and ring which is rotatable about a vertical axis and consists of a twin cylinder forming a hollow jacket filled with the chromatographic separation medium, and a mechanical drive. At its bottom end the rotating body is connected with a rotating platform which has vertical through channels and is guided sealingly and slidingly on a stationary eluate collecting ring with chambers. The rotating platform has an extension at its underside that can be coupled with a drive shaft of the drive by a rapidly detachable connection. The stationary column head, the rotating body with the rotating platform and the adjacent eluate collecting ring are combined into a CAC module and can be lifted as a unit from the drive shaft.

The rotatable and stationary parts of the device according to the invention form a unit that is independent of the drive and is held together by suitable means. The rotating body and the stationary parts of the device without the drive unit can be clamped into a kind of cage, for instance between plates, in order to secure a durable union, particularly of the sliding seal between the rotating body and the eluate collecting ring, even during manipulations such as removal from the drive or transport.

It is the purpose of this measure to have a chromatography device which together with the rotating body, the stationary column head and ports for liquid feed lines, the eluate collecting ring, the liquid drains of the chambers in the eluate collecting ring and, where applicable, the eluate collection vessel can be removed as a unit from the drive block, for instance, in order to sterilize it in an autoclave. However, the CAC device according to the invention preferably contains as well all design elements needed for a superheated-steam sterilization in situ, in the manner known particularly from fermentation technology, by passing saturated steam while the device is attached to the drive block. For a sterile process, preferably both the ducts feeding liquid to the column head and the ducts draining the chambers of the eluate collecting ring are provided with sterile connectors. For the feed ducts, for instance, standard sterile connectors such as the ones known from fermentation technology can be used. Additional sealing can also be used, particularly at the seams or contact points between components of the rotating body.

Shafts, V-belts, driving chains, toothed-wheel gearing and friction gear are suitable as a drive. The V-belt pulleys or gear rims can be mounted directly at the periphery of the rotating body; toothed wheels and friction wheels can also act on the inner wall of the rotating body having the shape of a cylinder jacket.

Drive shafts are preferred onto which the rotating body can be placed and to which it can be coupled. It is preferred here to couple the rotating body to the drive shaft, directly via a bottom plate shaped as a rotating platform immediately adjacent to the particle bed. To this end, the rotating platform has a short extension at its underside which is essentially of the same shape as the drive shaft and terminates into a sleeve which can be aligned with and pushed over the drive shaft so as to accept the torque of the drive shaft. Known torsion connectors and securities against twisting of the shafts can be used for coupling. Rigid coupling connectors for aligned shafts or radial serrations can for instance be used. What matters is that the rotating body can be removed from the drive shaft in a reversible and simple fashion without any demanding assembly work, and that the torque is reliably transmitted. Other coupling connectors suitable for connecting the rotating body to the drive shaft are known to one skilled in the art, and include plug-in, snap, slide-lock, catch, and screw connections.

At its coupling end, the drive shaft can be shaped in known fashion, for instance as a cylinder, cone, or polyhedron; the extension of the rotating platform to be attached to it must then be provided with an aligned sleeve having a complementary shape. Conversely, the drive shaft can terminate in a sleeve into which the extension of the rotating platform is precisely fitted with its end having a complementary shape.

The slide ring seal between the rotating platform and the stationary eluate collecting ring must always be compressed as needed so that the rotating body will be guided sealingly on the eluate collecting ring. The rotating body's own weight can provide the needed pressure. However, it is preferred according to the invention that one or several prestressed compression or tension springs are used. When prestressed tension springs are used, the eluate collecting ring is hung into them; when compression springs are used, they exert pressure from below on the eluate collecting ring. It is advantageous to provide pressure transfer pads with a pressure surface larger than the springs between the springs and the eluate collecting ring in order to distribute the spring force uniformly over the section of the eluate collecting ring.

The slide ring seal, the eluate collecting ring with its embedded chambers receiving the eluates draining from the particle bed, as well as the channels in the bottom plate or rotating platform can be realized in the fashion described initially, and known from WO 99/12625. However, in the present invention it is preferred to solve the problem of pressure fluctuations or underpressure described initally for the CAC device of WO 99/12625 in another way than by using pressure equalization ports in the chambers of the collecting ring.

In fact, it has surprisingly be found that hoses used as eluate withdrawal ducts from the chambers of the eluate collecting ring which where appropriate can be pushed over outlet sockets present at the chambers will solve the underpressure problem even without pressure equalization ports in the chambers, provided the hoses coming from the chambers or outlet sockets are made into siphons, by being for instance bent into a wave shape similar to a recumbent "S". It is unimportant then whether the hoses or eventual outlet sockets are attached to the bottom of the chambers and essentially point vertically down, or whether they are laterally attached to the chambers and preferably point outward and obliquely downward.

In this connection, it is decisive for optimum function of the CAC device according to the invention that between the particle bed and the siphons of the draining hoses a liquid through connection as in communicating vessels arises which despite rotation of the particle bed is preserved throughout the phases of elution and, where applicable, of washing and regeneration. For this reason it is not necessary either to keep the ends or highest portions of the draining hoses at a level below the chambers of the collecting ring, they rather can—and preferably should—be lifted to a level higher than the collecting ring and maintained there.

Apart from the invention being adapted for a sterilization in an autoclave, the modular structure of the device offers the advantage of simple interchangeability of the entire chromatography unit. Depending on the type of separation problem being dealt with, rotating bodies fully prepared can without waiting be placed one after the other onto the drive as complete chromatography units (modules) so that during a preparative CAC process, another module can already, for instance, be filled and conditioned in parallel.

It is not only possible to operate one and the same drive block with alternating chromatography modules, one also can adapt the hollow cylinder jackets containing the separation medium and the eluate outlets to the particular chromatographic job. For instance, hollow cylinder jackets or rotating bodies can be varied in their length by using the appropriate spacer rods of different length. The invention is also suited for compound bodies where several particle beds on top of each other or next to each other are used simultaneously for a separation, such as for instance described in WO 99/47913. By analogy, the basic idea and the principle of the present invention can be applied quite generally to all variants of particle beds and CAC devices such as disclosed in the international patent applications WO 98/45699, WO 99/12625, WO 99/29388, WO 99/28740, and WO 99/47913. The term "particle bed" should be understood here, not exclusively as a particulate chromatography gel or resin arranged in the hollow cylinder jacket of the rotating body but also as a monolithic separation medium suitable for liquid chromatography, for instance made of ceramic, plastic (for instance block polymer), fiber material and the like. The term also refers to a combination of two or several chromatographic separation media, where necessary in superimposed layers, preferably with separating layers in between, such as known from the precited publications.

BRIEF DESCRIPTION OF THE DRAWINGS

Below, the invention will be explained more closely in the instance of an embodiment while referring to the drawings. It is shown in.

DESCRIPTION OF THE PREFERRED EMBODIMENTS

Figure 1:
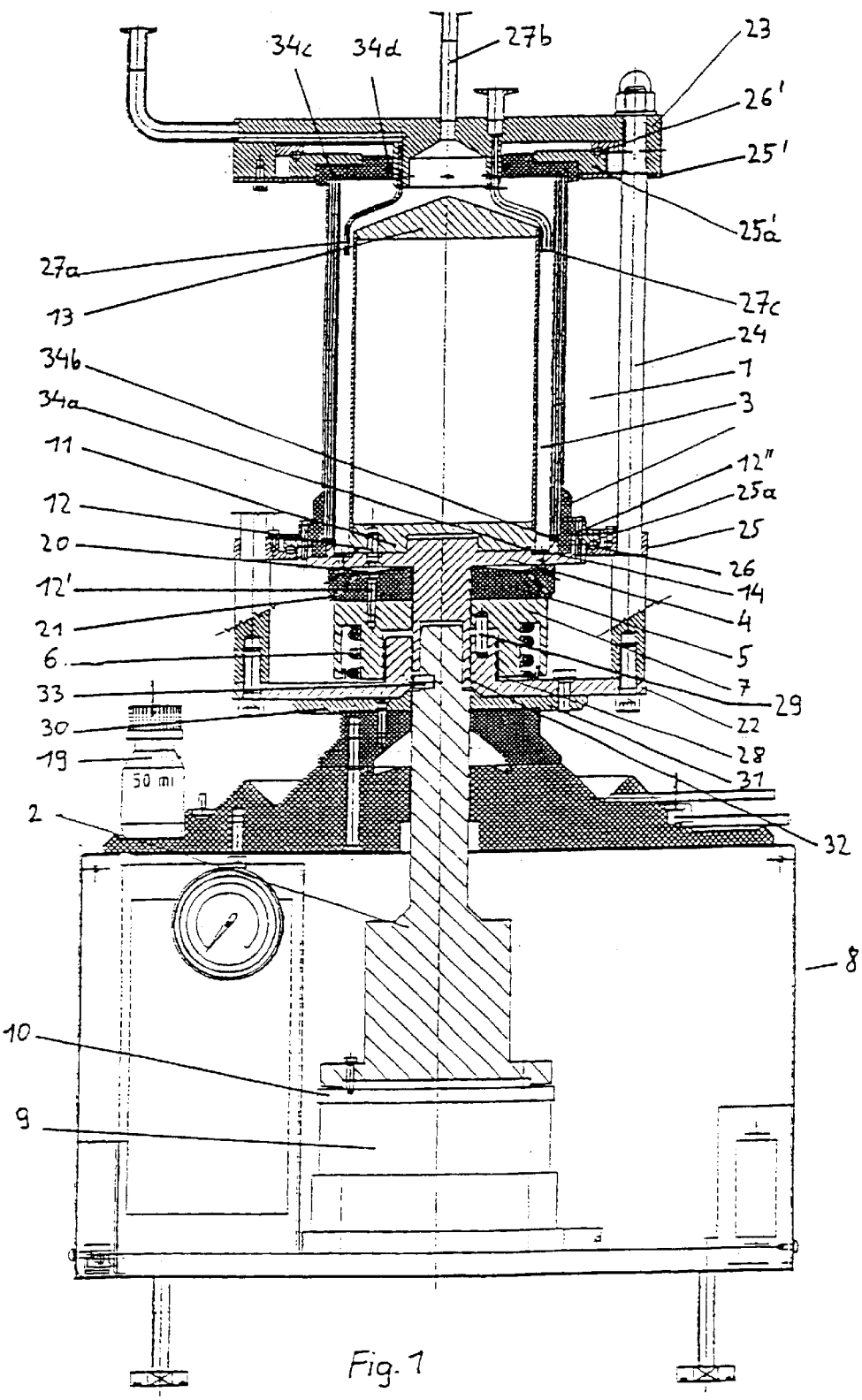
FIG. 1 a longitudinal section through the axis of rotation of a CAC device according to the invention.

In FIG. 1 a drive block 8 with drive shaft 2 connected with the rotor 10 of the motor 9 can be recognized. A rotating body 1 is placed on the drive shaft 2.

The rotating body 1 is closed toward the outside and serves to perform annular chromatography. At the rotating body 1, a hollow cylinder jacket constituting the particle bed space 3 supported by a rotating platform 4 is provided for receiving the particle bed. In the embodiment shown, the hollow cylinder jacket is placed upon the rotating platform 4 from above. As shown in this example, the inner cylinder of the hollow cylinder jacket can be connected below with a bottom support 11, and through this support it can be fixed at the rotating platform 4 via a screw connection 12, while above it can be closed off with a conical roof 13. For centering and stabilizing of the inner cylinder, the rotating platform 4 can have a central projection at its upper side which is aligned and engages with a recess in the underside of the bottom support 11 which is of complementary shape. It is advantageous for a contamination-free process to provide for additional seals 34a, 34b, 34c, 34d in the seams between the contacting portions of the components delimiting the particle bed space 3.

For torque transfer from the drive shaft 2, the rotating body 1 can be coupled with the drive shaft 2. To this end the rotating platform 4 has an extension at its underside which essentially has the shape of a central portion of the drive shaft 2, and at its end terminates into a sleeve 32 which can be aligned with and pushed over the free end of drive shaft 2 which by the lock-and-key principle has a shape complementary to that of sleeve 32. This coupling connection can be secured against twisting by a pin 33 laterally arranged in the drive shaft 2 and engaging into a corresponding recess of sleeve 32. Of course, the opposite version where the drive shaft ends into a sleeve into which an extension of the rotating platform 4 of complementary shape is engaged will be suitable as well and serve the same purpose.

A retaining strip or grid 14 inserted into the rotating platform 4 beneath the particle bed space 3 supports the particle bed and separates it from the adjoining channels 15 which preferably are expanded like wedges toward their upper ends, pass through the entire rotating platform 4, and convey the liquids draining from the particle bed to the chambers 16 (FIG. 2) of the eluate collecting ring 5. From the bottoms of chambers 16 of the eluate collecting ring 5 which, where necessary, are tapering like funnels or are beveled toward the outside, draining channels 17 (FIG. 2) lead out of the eluate collecting ring, and eluate drains 18 (FIG. 2) which in general are plastic hoses are attached to them in order to provide the connections—sterile, where necessary—between the eluate collecting ring 5 and the eluate collection vessels 19.

Figure 2:
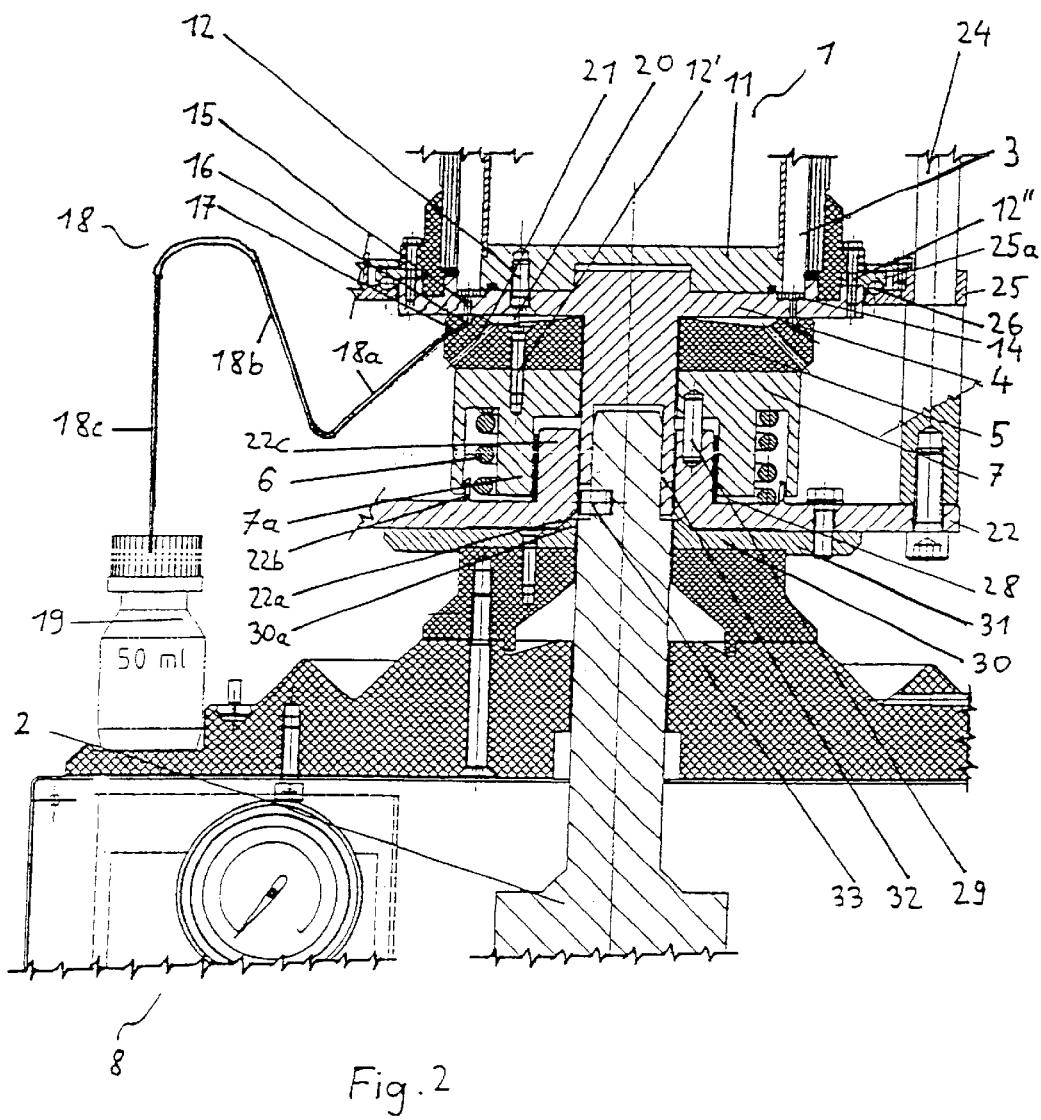
FIG. 2 a detailed view of the bottom region of the device of FIG. 1 with added representation of an eluate drain arranged in wave shape.

It is preferred to have eluate drains 18 laid out in wave shape like a recumbent "S", as shown in FIG. 2, in which case between a first part 18a of the eluate drain 18 running downward and the adjoining part 18b bent upward, a siphon is formed while the part 18c which follows next and is once more bent downward ends in an eluate collection vessel 19. This arrangement of the hoses of eluate drains 18 is readily brought about, for instance by lifting the hoses with a ring-shaped support surrounding the rotating body 1 which where necessary can be adjusted in its height (not shown in the figures).

When operating the CAC device as intended, between the particle bed space 3 and each eluate drain 18 a continuous liquid column is formed which is never completely broken because of the geometries of channels 15 in the rotating platform and of the radial walls between chambers 16 in the eluate collecting ring 5 which are specifically matched as discussed at the outset in the instance of WO 99/12625. By siphon formation in the eluate drains 18 according to the invention, it is secured that the liquid column starting in the particle bed will at least attain the siphon, and perhaps the upper bend of the wavelike eluate drains 18 that follows after the siphon, and thus a regular eluate flow is maintained. At the same time the chambers 16 are prevented from emptying completely and an underpressure cannot arise by a possible abrupt emptying of the chambers. Minor pressure fluctuations which still might occur are buffered by the liquid column in the eluate drains 18, so that an aspiration of (nonsterile) outside air through the slide ring seal cannot occur in any phase of the chromatographic operation.

For eluate drainage without contamination, the rotating platform 4 is guided slidingly and sealingly on two concentric gliding surfaces along the periphery of the eluate collecting ring 5, the chambers 16 being arranged between the gliding surfaces and the eluate collecting ring 5 being pressed against the rotating platfrom 4 by a helical spring 6. The helical spring 6 is centrally mounted so that the windings of the spring run around the axis of drive shaft 2. It transmits the spring force via a pressure pad 7 connected with the eluate collecting ring 5 by a screw connection 12' and acting as pressure transfer pad.

Between the inner gliding surface and the inner rim bordering the drive shaft, the eluate collecting ring 5 has a peripheral recess beveled toward the outside rim which with the underside of rotating platfrom 4 forms a hollow space 20; from the lowermost region of this space, one or several bores 21 lead from the eluate collecting ring 5 to the outside. On one hand the hollow space serves to delimit the size of the gliding surface, on the other hand it serves to enable superheated-steam sterilization of the gliding surfaces. The bores 21 then allow condensate accumulated during sterilization or during chromatograph operation (for instance when cooling to temperatures below room temperature) to be drained from this space.

It should be pointed out here that the CAC device according to the invention is preferably provided with means for temperature control and/or thermostatic operation, particularly with a heating and/or cooling circuit arranged inside and/or outside of the rotating body 1 in order to be able to create optimum operating conditions by heating or cooling for each chromatographic task and starting material employed. Temperature control can for instance be achieved with a liquid temperature control medium inside the inner cylinder of the rotating body 1 and/or by thermal insulation of the rotating body on its outside. The inner cylinder can also be realized as a twin jacket allowing circulation of the temperature control medium.

The rotating body 1 with rotating platform 4, stationary column head, eluate collecting ring 5, and pressure pad 7 with helical spring 6 is clamped between a torsionally rigid base plate 22 and a torsionally rigid head plate 23. The plates are screw-connected via separator rods 24 along their peripheries and are held at the desired distance by these rods. Approximately at the level of the rotating platform 4 along the separator rods 24, a step is provided which supports an axial bearing shell 25 with O-ring seal 26 on which an annular bearing runner 25a connected via a screw connection 12" with the rotating platform 4 is supported and guided slidingly.

The column head with supply ducts 27a, 27b, 27 for material feed, eluants, charging of particle bed material etc. having sterile connectors known from fermentation technology is integrated into the head plate 23 or connected with it as a single piece (as shown in the example of FIG. 1). The top part of the rotating body 1 which closes off the particle bed space 3 above is guided in the head plate 23 by a further axial sliding bearing via an O-ring seal 26' and annular bearing runner 25a' connected by bolts; the axial bearing shell 25' is solidly attached to the torsionally rigid head plate 23.

The base plate 22 has a central opening with an internal diameter approximately corresponding to the diameter of the drive shaft. The edges of this central opening develop into a cylinder jacket 22c rising vertically upward; its inner surface serves as guide sleeve for the extension 32 of the rotating platform 4. At the underside of base plate 22, the opening is expanded to a cone 22a substantially facilitating placing the CAC module onto the drive shaft 2. The cylinder jacket 22c in turn is surrounded by a slide seal collar 28 facilitating a vertical adjustment of base plate 22 relative to pressure pad 7. A pin 29 preventing the pressure pad 7 from turning relative to base plate 22 is slipped into the head portion of cylinder jacket 22c. The pressure pad 7 has a central through bore which in its diameter in a top portion adjacent to the eluate collecting ring 5 corresponds to the diameter of extension 32, and in the diameter in its adjacent portion corresponds to the diameter of cylinder jacket 22c including the collar 28, so that it can be pushed on one hand over the extension 32 of the rotating platform 4 and on the other hand over the collar 28 and the cylinder jacket 22c of the base plate. In a peripheral region 7a of pressure pad 7, an annular recess opening downward is provided which accepts the helical spring 6, the base plate 23 acting in this case as abutment for the helical spring 6. The pressure pad 7 is held at the base plate 22 but not fastened at it, hence the base plate 22 can be shifted or adjusted relative to this pad along the collar 28 in a vertical direction so that the spring pressure and thus the compression of the slide ring seal between eluate collecting ring 5 and rotating platform 4 can in any event be varied. A peripheral projection 22b projecting into the annular recess of cylinder jacket 7a is provided at the bottom plate 22 for further security. Finally, pressure pad 7 is solidly connected with the eluate collecting ring by a screw connection 12'.

The CAC module according to the invention, with the CAC device with rotating body 1, eluate collecting ring 5, pressure pad 7 and helical screw 6 clamped between base plate 22 and head plate 23, is placed onto a support plate 30 of the drive block 8. A central bore having its upper rim shaped as peripheral projection 30a that is complementary to the adjacent cone 22a of base plate 22 is provided in the support plate 30 to allow the drive shaft 2 to pass through. When the screw connection 31 between base plate 22 and support plate 30 is separated, the entire CAC module can simply be lifted from the drive block 8, where necessary with a crane, and autoclaved as such or replaced by another CAC module.

The CAC device according to the invention is basically suited for all current separation problems amenable to CAC or P-CAC, particularly those described for instance in WO 99/28740. This also includes the use of the most diverse chromatography gels or resins and combinations of such resins and gels, such as also described for instance in WO 99/28740. The use of monolithic separation media (for instance block polymer) or other separation media suited to liquid chromatography shall also be included here. The CAC device according to the invention is preferably employed for the purposes of preparative separation, purification and/or concentration of individual substances or mixtures of organic substances, particularly of proteins or protein mixtures of vegetal, animal (including human), or biotechnological origin (for instance, recombinant proteins) such as already quoted in part in WO 99/28740.

The sample material to be treated is introduced as a feed into the separation medium (for instance a particle bed of chromatography gel) at one point in the annular gap of the hollow cylinder jacket and conveyed by eluents (for instance chief eluent and step eluents) through the stationary phase, where adsorption and desorption processes can occur. Commonly, the chief eluent is applied in uniform distribution over the entire annular gap, for instance via the conical roof covering up the inner cylinder of the rotating body above, while the step eluent(s) are also introduced at specific points located at particular angular distances from the sample feed point, and distributed over the annular gap.

Apart from the supplies of feed and eluents, supplies of conditioning liquids, particularly washing, regenerating, and/or sanitizing agents can be present which can be arranged in front of, between, and/or behind the eluent inlets, depending on the type of processing job and sample material. This can be a considerable advantage or even a necessity when processing biological sample material often accompanied by numerous undesirable foreign substances, on one hand, and having organic components (for instance proteins) which are perishable and susceptible to infections, on the other hand. This is all the more true when dealing with materials subsequently to be used for medical purposes in man or animals.

It has now been realized that in some separation, purification, and particularly concentration jobs a procedure is advantageous where the supplies of sample feed and chief eluent are interchanged as compared with the traditional procedure, that is, by inverting the common approach, not the chief eluent but the sample material to be treated being applied while it is distributed over the entire annular gap. This approach makes sense, particularly when large volumes of sample material must be processed, for instance when a pharmaceutical active substance present at a very low concentration in a solution must be concentrated and/or purified from foreign substances.

Such problems can be handled much more economically with this "inverse" CAC method (also called "head-space" method) than with the traditional process variant, since the elution for instance can occur by easy and rapid desorption in a small angular segment or a small zone. For a selective desorption of the sample material adsorbed at the separation medium, one or several step eluent inlets and, when necessary, further inlets for washing, regenerating, and/or sanitizing agents are arranged at predetermined angular distances in front of, between, and/or behind the eluent inlets. Here it must be observed in certain cases that with elution and/or conditioning steps (for instance washing, regenerating, and/or sanitizing steps) to be performed in direct succession the corresponding supplies of elution and/or conditioning agents are arranged so close together that in between, sample material cannot enter the separation medium. As a complement or alternative, the flow rates of the sample-feed and detergent streams can be so adjusted relative to each other that the same effect is achieved.

It is preferred to this end to provide the column head with a multitude of extension tubes for the liquid feeds which are permanently mounted at short angular distances from each other. Of these, only a part is used and the others are closed off, depending on the separation task.

As an alternative, in another embodiment a smaller number of extension tubes are attached in mobile fashion at a guide ring (not shown in the figures) or annular guide rail above the annular gap of the hollow cylinder jacket, so that they can be shifted along the periphery of the ring or guide rail and fastened at the desired angular positions over the particle bed. To this end the extension tubes can be straight tubes. They preferably pass vertically through the guide ring or guide rail and are supported by glide or roll elements which are known for instance from sliding bearing technology and are fixed to the tubes.

For a vertical stabilization and immovable fixation at the guide ring or guide rail, the tubes can be tightened by screw or clamp connections beneath or above the guide ring or guide rail, or on both sides. In an analogous manner, other suitable suspension systems can be used for the tubes, so long as they allow the tubes to be shifted along the periphery of the annular gap above the particle bed. The tubes for instance can also be suspended in a mobile fashion with the aid of rings or ears at a single guide ring or at two superimposed guide rings, and fastened with suitable clamp connections. The guide rings or rails can also have locking positions where the tubes can be fixed in a stationary way. The connection between the tubes and the inlet ports in the column head is provided by flexible hoses of an inert material (for instance plastic), which may when necessary be armored, and can be attached to the tubes and the inlet ports in the column head by sleeves, plug-in, snap, or screw seals or similar detachable connecting means.

The optimum conditions for selecting or adjusting the angular positions, angular distances of the extension tubes, and/or flow rates of the liquid streams supplied can be determined by preliminary experiments for all preparative processing problems. This will be illustrated with the example following below.

EXAMPLE

Concentration of a Protein Solution by Inverse P-CAC

A solution essentially free of particles obtained from a fermentation for the microbial production of recombinant human factor VIII (abbreviated: rFVIII), for concentration of the rFVIII contained in it, is subjected to preparative continuous annular chromatography (P-CAC) using the CAC device according to the invention.

A CAC device is used which has a column head with seven inlets: a main inlet which distributes the sample material via the conical roof of the inner cylinder over the entire annular gap of the particle bed (except for those zones where elution or conditioning agents are introduced), and when necessary fills the entire head space of the rotating body with sample material, and one inlet each for washing and equilibrating solution (150 mM NaCl), eluent (0.7 M NaCl), regenerating agent (2 M NaCl), detergent (sodium lauryl sulfate), and sanitizing agent (1 M NaOH); in this example, one inlet remains idle.

A Poros DEAE anion exchanger gel (maker: Perspective Biosystems) is used as the particle bed in the hollow cylinder jacket of the rotating body, and covered with a layer of glass beads about 2–3 cm thick. All inlets except the main inlet are provided with appropriately bent extension tubes immersed into the glass bead layer and terminating about 0.5 to 1.5 cm above the gel bed of the anion exchanger. It is prevented in this way that the liquid streams discharged from the extension tubes directly "shoot" onto the gel bed and slurry up its uppermost region. Yet even when using glass beads as a protective layer and application aid, the flow rates of the liquids flowing through the extension tubes directly into the annular gap are relatively narrowly limited, so the introduction of the sample feed via one of these tubes would represent a rate-determining step. The problem was solved by the flooding of the head space with sample feed as provided by the invention.

For sterilization, the CAC module which has been fully charged and filled with deionized water or, when applicable, a washing liquid, is pinched off at the liquid feed ducts of the column head, or preferably tightly closed off with autoclavable membranes, particularly in the form of corresponding screw or plug-in connectors as known from fermentation technology. The hoses of the eluate drains of the collecting ring, preferably numbering between 90 and 180, are also tightly pinched off at their ends. They can also be provided with metal syringes facilitating an aseptic connection of the hoses with sterilized eluate collection vessels, where applicable containing a sealing membrane, for instance by piercing these membranes under flame protection. For the purposes of autoclaving, the syringes can in addition be protected by reusable protecting caps so as to further reduce the danger of contamination.

The stationary head plate closing off the rotating body above contains at least one more opening serving to enable a pressure equalization in the rotating body during autoclaving and thereafter in the phase of cooling. To this end the opening is covered by a sterile filter membrane which is autoclavable and permeable to air and humidity in both directions, for instance with a pore size of at most 0.45 $\mu$m, or alternatively with an in-depth filter system (for instance glass wool). Such pressure equalization systems are also sufficiently well known from fermentation technology. For autoclaving, the entire CAC module after unscrewing the screw(s) between base plate and rotating platform is lifted from the drive shaft of the motor drive, when necessary with a mobile crane, and placed into an autoclave of suitable size. The autoclaving which follows is performed in known fashion. For most practical applications, an exposure of 15 to 20 min at 120° C. (at a pressure of about 0.15 MPa or about 1.5 atm) will suffice.

The P-CAC Process

After autoclaving, cooling, and aseptic connection of the feed lines to the pumps, and of the eluate drain lines to the eluate collection vessels, preparative continuous annular chromatography was started by supplying the sample feed with a flow rate of 80 ml/min. The five inlet extension tubes for washing/equilibration, elution, regeneration, cleaning, and sanitizing were arranged so that they terminated in the glass bead layer of the annular gap within a single angular segment of 45°, thus hindering or completely preventing a penetration of sample material into the separation medium within the range of these angular positions. In this way it was guaranteed that behind the elution zone and between the conditioning zones, no sample material will contaminate the separation medium.

Figure 3:
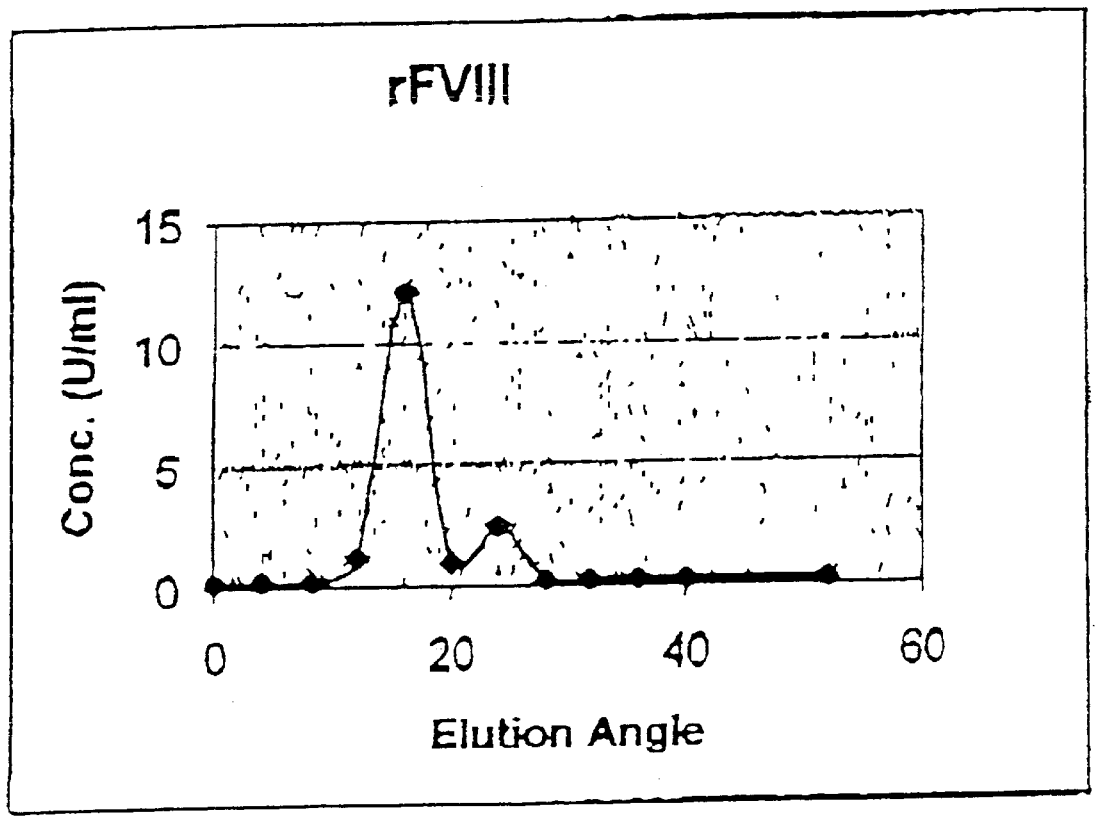
FIG. 3 a graphical representation of the result of a concentrating process using the CAC device according to the invention.

The flow rate for washing/equilibration was set to 4 ml/min, the other flow rates were each set to 2 ml/min. An angular velocity of 120 deg/h was selected as the rate of rotation for the rotating body. Sampling occurred after about 1.25 h. Despite processing conditions which were not yet optimum, a concentration of rFVIII by a factor of 13 was achieved (FIG. 3).

In another experiment the flow rates were changed, so that the sample feed occurred with 100 ml/min, washing/equilibration and elution with 3 ml/min each, regeneration, cleaning, and sanitizing with 2 ml/min each. At an angular velocity of 120 deg/h and a linear flow rate of 157 cm/h, collection of the fractions was started after 3 h. A concentration of the protein by a factor of 74 relative to the starting solution could be achieved (Table 1).

TABLE 1

Concentration of rFVIII by P-CAC

| Drain position | 1 | 2 | 3 | 4 | 5 | 6 | 7 | 8 | 9 |
|---|---|---|---|---|---|---|---|---|---|
| Titer [E/ml] | 0 | 74 | 24 | 9 | 0.3 | 2.3 | 0.3 | 0 | 0 |

The values are normalized to a starting solution with 0 E/ml.

What is claimed is:

1. Device for continuous annular chromatography (CAC) with a stationary column head, a stationary eluate collecting ring, between them a rotating body rotatable about a vertical axis and shaped as a twin cylinder forming a hollow jacket with a chromatographic separation medium contained therein, as well as a drive, the rotating body (1) being connected at its bottom end with a rotating platform (4) having vertical through channels (15) which is guided sealingly and slidingly on a stationary eluate collecting ring (5) with chambers (16), characterized in that the rotating platform (4) at its underside is provided with an extension that can be coupled to a drive shaft (2) of the drive (8) via a rapidly detachable connection, and the stationary column head, the rotating body (1) with rotating platform (4) and the adjacent eluate collecting ring (5) are combined into a CAC module and can be detached as a unit from the drive shaft (2).

2. Device according to claim 1, characterized in that at its end the extension of the rotating platform (4) is shaped into a sleeve (32) into which an end of the drive shaft (2) that is of complementary shape is engaged, or conversely, in that the drive shaft (2) at its end is provided with a sleeve into which an extension of the rotating platform (4) that is of complementary shape is engaged.

3. Device according to claim 1, characterized in that the column head, the rotating body (1) with rotating platform (4), and the eluate collecting ring (5) are clamped between a base plate (22) and a head plate (23), the base plate (22) and head plate (23) where applicable being held together by distance rods (24) arranged concentrically around the rotating body (1).

4. Device according to claim 3, characterized in that the column head has at least one liquid supply line (27).

5. Device according to claim 1, characterized in that the rotating platform (4) is supported by a peripheral axial bearing (25) borne by distance rods (24), and is slidingly guided on this bearing.

6. Device according to claim 1, characterized in that a pressure pad (7) pushing the eluate collecting ring (5) against the rotating platform (4) is arranged adjacent to the underside of the eluate collecting ring (5).

7. Device according to claim 6, characterized in that the pressure pad (7) in a peripheral region in a peripheral recess (7a) opening downward has a helical spring (6) acting as a compression spring wound concentrically around the drive shaft (2) and abutting the bottom plate (22) arranged directly beneath.

8. Device according to claim 1, characterized in that the rotating platform (4) rests on two concentric gliding surfaces on the eluate collecting ring (5) and the eluate collecting ring (5) between the inner gliding surface and its inner rim adjoining the drive shaft (2) has a recess beveled toward the outside which together with the rotating platform (4) forms a hollow space (20) from the lowest point of which at least one bore (21) leads from the eluate collecting ring (5) to the outside.

9. Device according to claim 1, characterized in that the eluate collecting ring (5) has a multitude of chambers (16) separated by radial walls, the thickness of each radial wall being smaller than the diameter of a channel (15) of the rotating platform (4).

10. Device according to claim 1, characterized in that eluate drain lines (18) are attached to the chambers (16) of the eluate collecting ring (5), these hoses first running downward, then bending up like a wave in the way of a recumbent "S", finally bending again downward and, where appropriate, terminating in eluate collection vessels (19), where the highest part of the eluate drain line (18).

11. Device according to claim 1, characterized in that the inner cylinder of the twin cylinder of the rotating body (1) at its lower end is solidly connected with a bottom support (11) which in turn rests on the rotating platform (4) and is connected immovably with it by at least one connecting element.

12. Device according to claim 1, characterized in that it has a number of extension tubes arranged in the head space above the separation medium and projecting into the annular gap of the hollow cylinder jacket of the rotating body (1), these tubes being connected with the inlet ports for the liquid supply lines (27a, 27c) and, where appropriate, able to be shifted in annular fashion along the periphery of the annular gap above the separation medium, and to be fixably arranged at desired angular positions.

13. Device according to claim 1, characterized in that it has means for temperature control and/or thermostatic operation.

14. Method for the purification, separation, and/or concentration of substances by means of liquid chromatography using a device for continuous annular chromatography (CAC) according to claim 1, characterized in that a liquid containing the substances is applied as sample material in uniform distribution over the entire periphery of a chromatographic separation medium present in a hollow cylinder jacket of a rotating body, with the stipulation that liquids for eluting the substances and conditioning the separation medium are applied to the separation medium at points situated at predetermined angular positions and that in the region of these positions a penetration of the sample material into the separation medium is hindered or prevented.

15. Method according to claim 14, characterized in that the sample material is supplied via a central inlet into a head space of the CAC device located above the separation medium.

16. Method according to claim 14, characterized in that the elution and/or conditioning liquids are applied above the separation medium at angular positions so selected that no sample material can pentrate into the separation medium between them.

17. Method according to claim 14, characterized in that the sample material contains organic substances.

18. Method according to claim 14, characterized in that the sample material contains recombinant human factor VIII and with the method a concentration of rFVIII by a multiple of the staffing concentration is accomplished.

19. Method according to claim 14, characterized in that the device for continuous annular chromatography is adjusted for aseptic operation.

20. Method according to claim 14, characterized in that the method comprises a step of steam sterilisation of the device for continuous annular chromatography, said step comprising autoclaving or super-heated steam sterilisation in situ.

* * * * *